United States Patent [19]

Husain et al.

[11] Patent Number: 4,956,494
[45] Date of Patent: Sep. 11, 1990

[54] OXIDATION OF THIOLS, DISULFIDES AND THIOLSULFONATES

[75] Inventors: Altaf Husain, East Norriton, Pa.; Gregory A. Wheaton, Logan Township, Gloucester County, N.J.

[73] Assignee: Pennwalt Corporation, Philadelphia, Pa.

[21] Appl. No.: 366,350

[22] Filed: Jun. 15, 1989

Related U.S. Application Data

[63] Continuation of Ser. No. 112,648, Oct. 26, 1987, abandoned.

[51] Int. Cl.$^5$ .................... C07C 139/00; C07C 51/58
[52] U.S. Cl. ........................................ 562/118; 562/828
[58] Field of Search ................................ 562/118, 828

[56] References Cited

U.S. PATENT DOCUMENTS

| | | | |
|---|---|---|---|
| 1,925,191 | 9/1933 | Keller | 260/513 R |
| 1,966,187 | 7/1934 | Schirm | 260/513 R |
| 2,489,316 | 11/1949 | Proell | 260/513 R |
| 3,248,423 | 4/1966 | Stratton | . |
| 3,509,206 | 4/1970 | Nielsen | . |
| 3,626,004 | 12/1971 | Guertin | . |
| 3,948,922 | 4/1976 | Lowe | 260/513 R |
| 4,052,445 | 10/1977 | Schreyer et al. | . |
| 4,239,696 | 12/1980 | Schreyer et al. | 260/513 R |
| 4,286,966 | 7/1981 | Hübenett | . |

FOREIGN PATENT DOCUMENTS 0040560 11/1981 European Pat. Off. .

Primary Examiner—Alan Siegel

[57] ABSTRACT

Alkanesulfonic acids and alkanesulfonyl chlorides, free of undesirable side products arising from side-chain chlorination, are prepared by oxidation with hydrogen peroxide of the corresponding alkanethiol, dialkyldisulfide or alkyl alkanethiolsulfonate mixed with aqueous hydrochloric acid.

13 Claims, No Drawings

OXIDATION OF THIOLS, DISULFIDES AND THIOLSULFONATES

This is a continuation of application Ser. No. 0/112,648 filed on Oct. 26, 1987 now, abandoned.

BACKGROUND

This invention relates to the manufacture of alkanesulfonic acids and alkanesulfonyl chlorides by oxidation of the corresponding alkanethiol, dialkyldisulfide or alkyl alkanethiolsulfonate. More particularly, it relates to the oxidation of such corresponding compounds in mixtures of hydrogen peroxide and hydrogen chloride to form alkanesulfonic acids and alkanesulfonyl chloride free of undesirable side products arising from side-chain chlorination of the alkyl group as commonly observed in direct chlorine oxidation.

PRIOR ART

The most commonly used method for the manufacture of alkanesulfonic acids or alkanesulfonyl chlorides involves oxidation of corresponding alkanethiol or dialkyldisulfide by chlorine in concentrated hydrochloric acid media (e.g., U.S. Pat. Nos. 626,004; 4,280,966 and EP No. 0,040,560) according to the following proposed equations:

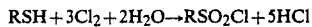

$RSH + 3Cl_2 + 2H_2O \rightarrow RSO_2Cl + 5HCl$

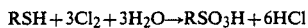

$RSH + 3Cl_2 + 3H_2O \rightarrow RSO_3H + 6HCl$

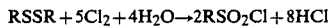

$RSSR + 5Cl_2 + 4H_2O \rightarrow 2RSO_2Cl + 8HCl$

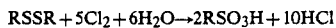

$RSSR + 5Cl_2 + 6H_2O \rightarrow 2RSO_3H + 10HCl$

A problem associated with the direct chlorine oxidation method is the formation of undesirable side-products arising from the chlorination of the alkyl side-chain. This problem becomes particularly serious in the manufacture of higher alkanesulfonic acids and alkanesulfonyl chlorides (C₃ and higher) due to the ease of direct side-chain chlorination. Because of the inherent thermal instability of alkanesulfonyl chlorides, it is extremely difficult to purify the crude product resulting from direct chlorine oxidation.

Another problem with the direct chlorine oxidation method is the large amount of by-product hydrochloric acid produced in the process. For each mole of alkanesulfonyl chloride, four and five moles of hydrochloric acid are produced using dialkyldisulfide and alkanethiol, respectively. Similarly, for each mole of alkanesulfonic acid, five and six moles of hydrochloric acid are produced using dialkyldisulfide and alkanethiol respectively. This causes a severe disposal problem both from economic and environmental considerations.

A method has previously been proposed to form (C₄-C₂₀) alkanesulfonyl chlorides with decreased side-products resulting from side-chain chlorination of the alkyl group wherein the corresponding alkanethiol or dialkyldisulfide is oxidized by a mixture of a small amount of oxygen in chlorine gas introduced to a mixture of a thiol or disulfide suspended in aqueous hydrogen chloride (See U.S. Pat. No. 3,248,423). While this method apparently decreases the formation of unwanted side-products in the preparation of C₄ and higher alkanesulfonyl chlorides as compared to the direct chlorine oxidation method, appreciable quantities of the side-product are shown to be formed. In addition, this method suffers from the disadvantage that a large amount of hydrogen chloride is formed as a by-product of the oxidation reaction.

STATEMENT OF THE INVENTION

This invention is a process for preparing alkanesulfonic acids and alkanesulfonyl chlorides comprising contacting an alkanethiol, a dialkyldisulfide or an alkyl alkanethiolsulfonate in aqueous hydrochloric acid with hydrogen peroxide to produce the corresponding alkanesulfonic acid or alkanesulfonyl chloride.

DETAILED DESCRIPTION OF THE INVENTION

The method of this invention involves oxidation of an organosulfur reactant selected from alkanethiols, dialkyldisulfides and alkyl alkanethiolsulfonates with a combination of hydrogen peroxide and hydrochloric acid according to the following chemical equations:

$RSH + 3H_2O_2 + HCl \rightarrow RSO_2Cl + 4H_2O$

$RSSR + 5H_2O_2 + 2HCl \rightarrow 2RSO_2Cl + 6H_2O$

$RSO_2SR + 3H_2O_2 + 2HCl \rightarrow 2RSO_2Cl + 4H_2O$

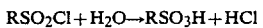

$RSO_2Cl + H_2O \rightarrow RSO_3H + HCl$

The alkanethiols that are employed in the present invention have 1–18 carbon atoms, preferably 1–8 carbon atoms. Thus, there is used, for example, methanethiol, ethanethiol, n-propanethiol, isopropanethiol, 1-butanethiol, 2-butanethiol, 1-hexanethiol, 1-octanethiol or 1-decanethiol. As the dialkyldisulfide, there is used, for example, compounds having 2–20 carbon atoms combined in the alkyl moieties, preferably 2–16 carbon atoms. For example, dimethyl disulfide, diethyl disulfide, dipropyl disulfide, diisopropyl disulfide, dibutyl disulfide, diamyl disulfide, dihexyl disulfide, dioctyldisulfide, or didecyl disulfide are used. As the alkyl alkanethiolsulfonate there is used, for example, compounds having 2–20 carbon atoms in the combined alkyl and alkane moieties, preferably 2–16 carbon atoms. For example, methyl methanethiolsulfonate, ethyl ethanethiolsulfonate, propyl propanethiolsulfonate, isopropyl isopropanethiolsulfonate, butyl butanethiolsulfonate, pentyl pentanethiolsulfonate, hexyl hexanethiolsulfonate, octyl octanethiolsulfonate and decyl decanethiolsulfonate are used.

The concentration of peroxide in the aqueous hydrogen peroxide solution that can be employed can range from 3 weight percent to 90 weight percent; however, concentrations of about 30 weight percent to 70 weight percent hydrogen peroxide, because of its availability, are preferred.

The amount of hydrogen peroxide used in the process of this invention can range from about 3–4 moles for each mole of alkanethiol or alkyl alkanethiolsulfonate and about 5–6 moles for each mole of dialkyldisulfide. Preferably, the amount of hydrogen peroxide used is about 3.3 moles for each mole of alkanethiol or alkyl alkanethiolsulfonate and about 5.5 moles for each mole of dialkyldisulfide.

The concentration of hydrogen chloride in the aqueous hydrochloric acid solution that can be employed is from 10 weight percent to 38 weight percent. Preferably, the concentration of hydrogen chloride is about 36–38 weight percent.

The amount of hydrogen chloride used can range from 1–10 moles for each mole of alkanethiol or from 2–20 moles for each mole of dialkyldisulfide or alkyl alkanethiolsulfonate. Preferably, the amount of hydrogen chloride used is between about two and four moles for each mole of alkanethiol and between about four and six moles for each mole of dialkyldisulfide or alkyl alkanethiolsulfonate.

The temperature at which the process of this invention is carried out can vary from about 0° C. to about 60° C. Preferably the temperature is between 25°–35° C. for the preparation of alkanesulfonyl chloride and between 50°–60° C. for the preparation of alkanesulfonic acid.

The manner in which the process of this invention is carried out depends upon the individual organosulfur reactant employed and the product desired. In general, when alkanesulfonyl chloride is the desired product, aqueous hydrogen peroxide is added slowly to a mixture of alkanethiol (or dialkyldisulfide or alkyl alkanethiolsulfonate as the case may be) and aqueous hydrochloric acid over a period of one to two hours while the temperature is raised from 0° C. to 35° C. over the addition period. The reaction mixture is stirred at 35° C. for an additional one or two hours. After this time, the reaction mixture is cooled and extracted with a suitable organic solvent such as, methylene chloride, chloroform, carbon tetrachloride, toluene, or equivalent solvent. The resultant organic extract is evaporated to obtain the alkanesulfonyl chloride. In most cases the product alkanesulfonyl chloride separates out as a lower layer. If desired the process of this invention can be run in a continuous manner by removing the lower product layer and charging fresh feed.

Similarly, if the desired product is alkanesulfonic acid, aqueous hydrogen peroxide is added to a mixture of alkanethiol (or dialkyldisulfide or alkyl alkanethiolsulfonate as the case may be) and aqueous hydrochloric acid over a period of one to two hours while the temperature is raised from 0° C. to about 60° C. over the addition period. The reaction mixture is stirred at 60° C. for an additional one or two hours. The desired concentration of alkanesulfonic acid can then be produced from the product mixture by methods known to those skilled in the art.

The process of this invention is demonstrated in the following examples.

EXAMPLE 1

There was added, with vigorous stirring using a mechanical stirrer, 62.3 g of 30 weight percent aqueous hydrogen peroxide (550 mmole) to a mixture of 9.4 g of dimethyldisulfide (100 mmole) and 50 g of 36.5 weight percent aqueous hydrochloric acid (500 mmole) over a period of one and one-half hours while the reaction temperature was increased from 5° C. to 35° C. The reaction mixture was stirred at 35° C. for an additional hour. The reaction mixture was then cooled to about 25° C. and extracted with three 25 ml aliquots of methylene chloride. Analysis of the methylene chloride extract by gas chromatography indicated that no detectable products arising from the side chain chlorination are formed. The organic extract was evaporated using a rotary evaporator, and the resulting product was distilled under reduced pressure to obtain 5.1 g of pure methanesulfonyl chloride.

EXAMPLE 2

There was added, with vigorous stirring using a mechanical stirrer, 62.3 g of 30 weight percent aqeuous hydrogen peroxide (550 mmole) to a mixture of 15.0 g of di-n-propyl-disulfide (100 mmole) and 50 g of 36.5 weight percent aqueous hydrochloric acid (500 mmole) over a period of one and one-half hours while the reaction temperature was increased from 5° C. to 35° C. The reaction mixture was stirred at 35° C. for an additional one hour. The reaction mixture was then cooled and extracted with three 25 ml portions of methylene chloride. Analysis of the methylene chloride extract by gas chromatography indicated that no detectable products arising from the side-chain chlorination are formed. From the methylene chloride extract, 16.9 g. (118.3 mmoles) of pure n-propanesulfonyl chloride was isolated in the same manner as in Example 1.

EXAMPLE 3

60 g of 30 weight percent aqueous hydrogen peroxide (530 mmole) was added, with vigorous stirring using a mechanical stirrer, to a mixture of 23.4 g of 1-octanethiol (160 mmole) and 50 g of 36.5 weight percent aqueous hydrochloric acid (500 mmole) over a period of two hours while the reaction temperature was increased from 25° C. to 50° C. The reaction mixture was stirred for an additional one hour at 50° C. The reaction mixture was then cooled and extracted with three 25 ml portions of methylene chloride. Analysis of the methylene chloride extract by gas chromatography indicated that no detectable products arising from the side-chain chlorination are formed. From the organic extract 14.7 g of pure 1-octanesulfonyl chloride was obtained in the same manner as described in Example 1.

EXAMPLE 4

There was added with vigorous stirring using a mechanical stirrer 62.3 g of 30 weight percent aqueous hydrogen peroxide (550 mmoles) to a mixture of 9.4 g of dimethyldisulfide (100 mmole) and 50 g of 36.5 weight percent aqueous hydrochloric acid (500 mmole) over a period of one and one-half hours while the reaction temperature was increased from 5° C. to 60° C. The reaction mixture was stirred at 60° C. for an additional hour. After this time the reaction mixture was cooled to room temperature. In this manner 13.4 g of methanesulfonic acid was obtained as analyzed by ion chromatography. No products arising from the side-chain chlorination are detected.

EXAMPLE 5

There was added with vigorous stirring using a mechanical stirrer 37.4 g of 30 weight percent aqueous hydrogen peroxide (330 mmoles) to a mixture of 12.6 g of methyl methanethiolsulfonate (100 mmole) and 50 g of 36.5 weight percent aqueous hydrochloric acid (500 mmoles) over a period of one and one-half hours while the reaction temperature was increased from 5° C. to 35° C. The reaction mixture was stirred for an additional one hour at 35° C. After this stirring time, the reaction mixture was cooled and extracted with three 25 ml. portions of methylene chloride. Analysis of the methylene chloride extract by gas chromatography indicated that no detectable products arising from side-chain chlorination are formed. From the organic extract, 15.63 g of pure methanesulfonyl chloride was obtained in the same manner as described in Example 1.

For comparison with the results of the above examples, the following described reaction demonstrates the formation of side-chain chlorinated impurities in the preparation of n-propanesulfonyl chloride by reaction of n-propanethiol with chlorine in a concentrated aqueous hydrochloric acid medium as known in the prior art. n-propanethiol (5.50 gms) was added to 70 mls (80.90 gms) of concentrated hydrochloric acid (37.4 weight-% HCl) in a five-necked, tapered flask equipped with a sintered-glass gas dispersion tube, a mechanical stirrer, thermometer, and a reflux condenser. The flask was immersed in a water bath at 20° C. and chlorine was introduced through the gas dispersion tube beneath the surface of the liquid at a rate of about 40 mls/min with vigorous mechanical mixing for a period of one hour. The product mixture was extracted with three 25 ml. portions of methylene chloride. Analysis of the organic extract by gas chromatography indicated that n-propanesulfonyl chloride was produced in 95% yield but that it contained 1.35 weight-% of a mixture of 1-chloropropanesulfonyl chloride and 3-chloropropanesulfonyl chloride as impurities.

We claim:

1. A process for preparing alkanesulfonic acids and alkanesulfonyl chlorides comprising contacting an alkanethiol, a dialkyldisulfide or an alkyl alkanethiolsulfonate mixed in aqueous hydrochloric acid with hydrogen peroxide to produce the corresponding alkanesulfonic acid or alkanesulfonyl chloride, the concentration of hydrogen chloride being from 10 to 38 percent based on the weight of said aqueous hydrochloric acid and the amount of hydrogen chloride used ranges from 1 to 10 moles for each mole of alkanethiol and from 2 to 20 moles for each mole of dialkyldisulfide or alkyl alkanethiolsulfonate.

2. The process of claim 1 wherein the alkanethiol has from 1 to 18 carbon atoms, the dialkyldisulfide has from 2 to 20 carbon atoms, the alkyl alkanethiolsulfonate has from 2 to 20 carbon atoms, and the temperature is from about 0° to 60° C.

3. The process of claim 2 wherein said hydrogen peroxide is used in an amount ranging from about 3 to 4 moles for each mole of alkanethiol or alkyl alkanethiolsulfonate and from about 5 to 6 moles for each mole of dialkyldisulfide.

4. The process of claim 3 wherein said hydrogen peroxide is in the form of an aqueous solution at a concentration ranging from 3 to 90 percent based on the weight of the solution.

5. The process of claim 2 wherein the hydrogen peroxide is in the form of an aqueous solution at a concentration ranging from 3 to 90 percent based on the weight of the solution and is present in an amount of from about 3 to 4 moles for each mole of alkanethiol or alkyl alkanethiolsulfonate and from about 5 to 6 moles for each mole of dialkyldisulfide.

6. The process of claim 5 wherein the alkanethiol has from 1 to 8 carbon atoms, the dialkyldisulfide has from 2 to 16 carbon atoms and the alkyl alkanethiolsulfonate has from 2 to 16 carbon atoms.

7. The process of claim 6 wherein the hydrogen peroxide concentration used in 30-70 weight percent and the amount of hydrogen peroxide present is about 3.3 moles, the hydrogen chloride concentration is about 36 to 38 percent and the amount of hydrogen chloride used ranges from about 2 to 4 moles for each mole of alkanethiol and about 4 to 6 moles for each mole of dialkyldisulfide or alkyl alkanethiolsulfonate.

8. A process for preparing alkanesulfonic acids comprising contacting with hydrogen peroxide a mixture of an alkanethiol having from 1 to 8 carbon atoms, a dialkyldisulfide having from 2 to 16 carbon atoms or an alkyl alkanethiolsulfonate having from 2 to 16 carbon atoms with an aqueous hydrochloric acid solution having a hydrogen chloride concentration of 36 to 38 percent based on the weight of said solution and in an amount of about 2 to 6 moles of hydrogen chloride per mole of alkanethiol, dialkyldisulfide or alkyl alkanethiolsulfonate, and the temperature of the process is between 50° and 60° C.

9. The process of claim 8 wherein the amount of hydrogen peroxide used is about 3.3 moles per mole of alkanethiol or alkyl alkanethiolsulfonate, or about 5.5 moles per mole of dialkyldisulfide.

10. The process of claim 9 wherein said hydrogen peroxide is in the form of an aqueous solution at a peroxide concentration of about 30 to 70 percent based on the weight of said solution.

11. A process for preparing alkanesulfonyl chlorides comprising contacting with hydrogen peroxide a mixture of an alkanethiol having from 1 to 8 carbon atoms, a dialkyldisulfide having from 2 to 16 carbon atoms or an alkyl alkanethiolsulfonate having from 2 to 16 carbon atoms with an aqueous hydrochloric acid solution having a hydrogen chloride concentration of 36 to 38 percent based on the weight of said solution and in an amount of about 2 to 6 moles of hydrogen chloride per mole of alkanethiol, dialkyldisulfide or alkyl alkanethiolsulfonate, and the temperatures of the process is between 25° and 35° C.

12. The process of claim 11 wherein the amount of hydrogen peroxide used is about 3.3 moles per mole of alkanethiol or alkyl alkanethiolsulfonate, or about 5.5 moles per mole of dialkyldisulfide.

13. The process of claim 12 wherein said hydrogen peroxide is in the form of an aqueous solution at a peroxide concentration of about 30 to 70 percent based on the weight of said solution.

* * * * *